United States Patent
Grundei

(10) Patent No.: US 6,413,261 B1
(45) Date of Patent: Jul. 2, 2002

(54) SYSTEM FOR RECONSTRUCTING THE TWIST BETWEEN THE NATURAL KNEE AND THE REGION OF THE NATURAL HIPS

(75) Inventor: Hans Grundei, Lübeck (DE)

(73) Assignee: ESKA Implants GmbH & Co., Lübeck (DE)

(*) Notice: Subject to any disclaimer, the term of this patent is extended or adjusted under 35 U.S.C. 154(b) by 146 days.

(21) Appl. No.: 09/585,145

(22) Filed: Jun. 1, 2000

Related U.S. Application Data

(63) Continuation of application No. PCT/EP98/05837, filed on Sep. 15, 1998.

(30) Foreign Application Priority Data

Dec. 1, 1997 (DE) .......................... 197 53 236

(51) Int. Cl.$^7$ ................................. A61F 5/00
(52) U.S. Cl. ..................... 606/87; 606/88; 606/96
(58) Field of Search .................... 606/80, 87, 88, 606/89, 96; 623/20.14, 20.15, 20.16

(56) References Cited

U.S. PATENT DOCUMENTS

| | | | |
|---|---|---|---|
| 5,047,058 A | * 9/1991 | Roberts et al. | ......... 623/20.14 |
| 5,364,401 A | 11/1994 | Ferrante et al. | |
| 5,417,694 A | * 5/1995 | Marik et al. | .............. 606/88 |
| 5,486,178 A | * 1/1996 | Hodge | ................... 606/88 |
| 5,916,220 A | * 6/1999 | Masini | ................... 606/88 |

FOREIGN PATENT DOCUMENTS

EP 0 709 061 A1 5/1996

* cited by examiner

Primary Examiner—David O. Reip
Assistant Examiner—Julian W. Woo
(74) Attorney, Agent, or Firm—Akin, Gump, Strauss, Hauer & Feld, L.L.P.

(57) ABSTRACT

The system includes a nail jig which is initially secured by means of fixing nails (38), after production of a stable three-point mounting of plates and legs extending from the nail jig, on the femur (10) in the vicinity of the condyles of the knee joint. The nail jig can then be removed from the femur (10), leaving the fixing nails (38) in the femoral bone. A saw jig (40) with the same basic shape as the nail jig and with identical holes for the fixing nails (28) can be placed on the fixing nails which were left in the femur (10). Precise allocation of boring pairs by both the nail and saw jig enables twist to be transferred to the artificial knee joint system at a ratio of 1:1 according to the predetermined size of the part of the femur to be implanted. In order to compensate for the incline in the frontal resection surface which is attached at a slant, the system is provided with a compensating wedge (46) which is inserted between the striking plate (32) and the lateral condyle (39'). The compensating wedge angle is similar to the angle of the horizontal resection surface in relation to the axis of the gap in the knee.

4 Claims, 6 Drawing Sheets

SYSTEM FOR RECONSTRUCTING THE TWIST BETWEEN THE NATURAL KNEE AND THE REGION OF THE NATURAL HIPS

CROSS REFERENCE TO RELATED APPLICATION

This application is a continuation of International Application PCT/EP98/05837, filed Sep. 15, 1998, the disclosure of which is incorporated herein by reference.

BACKGROUND OF THE INVENTION

The present invention relates to a system for the reconstruction of the natural twist between the natural knee and the region of the natural hips in an arrangement between an artificial knee joint and the region of the natural hips after partial resection of the natural condyles of the knee joint and bearing of a part of the femur of the artificial knee joint of a certain size on the resection surfaces of the femur bone, as is described in the applicant's not previously published German patent application 197 16 300.9-35.

By twist is understood a rotation of the femur bone into itself, which can lead to an angle, which is individually different for every person, between the knee joint on the one hand, and the neck of the thigh and hip head, on the other hand, which decisively influences running behavior and animation.

Should the replacement of the natural knee joint by an artificial total replacement implant now prove to be necessary, for example as a result of a tumor infection, the natural joint parts must be partially resected and replaced by implant components. If the femoral resection is performed in a traditional manner, it can be the case that the femoral components of the artificial knee joint stand at an angle to the hip region that is changed from the angle of the natural knee joint prior to the resection, i.e., as a result, that the natural twist is no longer found in the overall system of the femur after the operation. A changed running behavior and a changed animation of the patient is the direct result.

Before a femur part can be applied on the femur, generally a horizontal bearing surface is first made by resection of the sliding part of the condyles using an appropriate saw. After that, the ventral and dorsal sections as well as the two diagonal sections which connect them to the horizontal bearing surface are also missing.

A device for fixing resection surfaces on the femur and on the tibia for preparation of an implantation of a knee joint total endoprosthesis is known from German patent DE 44 23 717. In this patent, the main point focuses on the ventral section and dorsal section on the femur being made exactly parallel to the frontal resection surface on the tibia. This patent does not give any indication with regard to a possible rotational angle in the production of the resection surfaces, so that when the device disclosed in this patent is handled improperly, the twist after the operation is completely different from the previous one. However, this cannot be readily corrected, particularly since at least one additional serious operation would be necessary.

SUMMARY OF THE INVENTION

With the described system, one proceeds such that the frontal section on the tibia is carried out horizontally. The horizontal plane is then shifted in parallel, for example through a parallel plane according to German patent DE 44 23 717, and reproduced on the femoral bone, so that the front femoral resection cut also lies horizontally.

It is proposed that the system have a nail jig with an exactly cuboid (i.e., rectangular parallelepiped in shape) bearing block, which has on its end face seen ventrally a leg projecting therefrom pointing toward the femur, which holds on its end a femur contact feeler in the form of a bolt standing perpendicular to the leg for ventrally lying point support on the femur, and has on its face seen dorsally at least one striking plate projecting therefrom and pointing toward the femur for respective dorsally lying point support on both dorsal condyle rounds (i.e., the femoral part of the knee joint), wherein the bearing block has drill hole pairs passing through it. The arrangement of the drill holes represents the respective size of the femur part, through which fixing nails can be inserted, which secure the bearing block in its position on the femur, and whereby the bearing block can be pulled away from the femur while leaving the fixing nails behind. The system also has a saw jig with an identical basic shape as the bearing block of the nail jig and with an identical arrangement of drill hole pairs in the bearing block, which can be set on the fixing nails so that its face sides define the remaining resection planes.

The connecting components between the nail jig and the saw jig are accordingly the fixing nails, which fit in drill hole pairs both in the bearing block and in the saw jig—depending on the size of the joint, so that the position of the nail jig is converted to the position of the saw jig on the femur stump. Prerequisite for the application of the system is first the production of a horizontal bearing surface for the femur part of the artificial hip joint. The sliding parts of the natural condyles are thereby removed. In approximately 90% of operation cases, the dorsal condyle rounds remain undamaged and can thus be used as a reference point for the determination of the twist. The starting point for consideration in the system is that first a stable three-point bearing is in a position to form a stable system for reproducing the twist. Two of the three points are specified by the dorsally lying contact points of the above-mentioned striking plate on the two condyle rounds.

The still missing third point for the three-point bearing of the nail jig is determined by the femur contact feeler, which takes care of a point-shaped contact with the femur on the opposite side, i.e., ventrally located.

The surgeon must next—after the size of the femur part to be implanted has been clearly determined—produce the horizontal bearing surface on the femur, and then set the nail jig on the femur stump in such a way that a stable three-point bearing of the nail jig occurs on the femur stump by virtue of the femur contact feeler and the at least one striking plate for the two condyle rounds.

After producing the stable three-point bearing of the nail jig, the surgeon fixes it onto the horizontal bearing surface using two fixing nails, which he strikes through the pair of drill holes corresponding to the size of the implant and through the bearing block into the femur bone. After that, the nail jig is pulled away from the femur leaving behind the fixing nails, and the above-mentioned saw jig is set on the fixing nails still sticking in the femur. The reproduction of the twist is accomplished based on the identical basic shape of the saw jig as the nail jig and the identical arrangement of the drill hole pairs in the saw jig as in the nail jig. After setting the saw jig on the fixing nails and, if necessary, an additional affixing of the saw jig, the remaining resection sections are then carried out according to the specification of the saw jig. In particular, this involves the dorsal section, the ventral section and the two diagonal sections, such that the thus-produced diagonal section surface connects the horizontal bearing surface with the dorsal or ventral resection surface. Thus, the femur part of the artificial hip joint can be affixed: to the corresponding bearing surfaces on the femur, with or without bone cement.

A typical femur part for an artificial hip joint having corresponding bearing surfaces is likewise shown in German published patent application DE-A-41 41 757.

There is also another starting point for the present invention:

Fundamentally, the system of German patent application 197 16 300.9-35 is based on the reference of the frontal horizontal section on the tibia as well as of the bearing point of a striking plate on the rear condyle rounds of the femur.

Added to this is the fact that;the lateral condyle of the femur lies higher than the medial condyle. The hypothetical connection line from lateral to medial between the two condyles thus slopes relative to the horizontal. This leads to the consideration that the resection surface on the tibia should also be a surface sloping relative to the horizontal, in order to generate as natural conditions as possible in the artificial knee joint. Of course, the question then arises of how the described system can still be used, since this proceeds from the assumption of horizontal sections.

BRIEF DESCRIPTION OF SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings.

In the Figures, like elements are always provided with the same reference numerals.

DETAILED DESCRIPTION OF THE INVENTION

Figure 2:
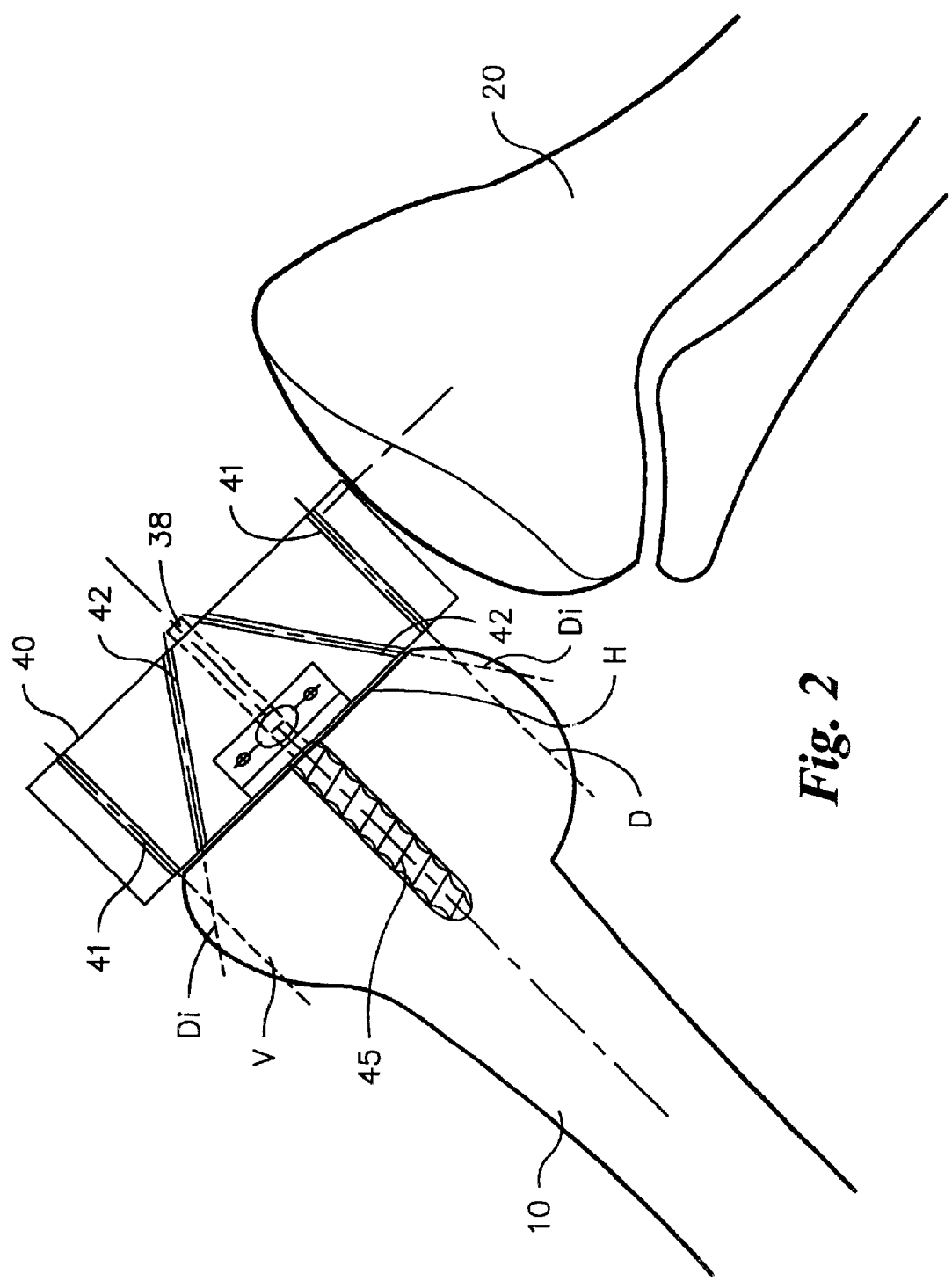
FIG. 2 is the view of the partially resected natural knee joint from the medial with the saw jig set on it.
Figure 3:
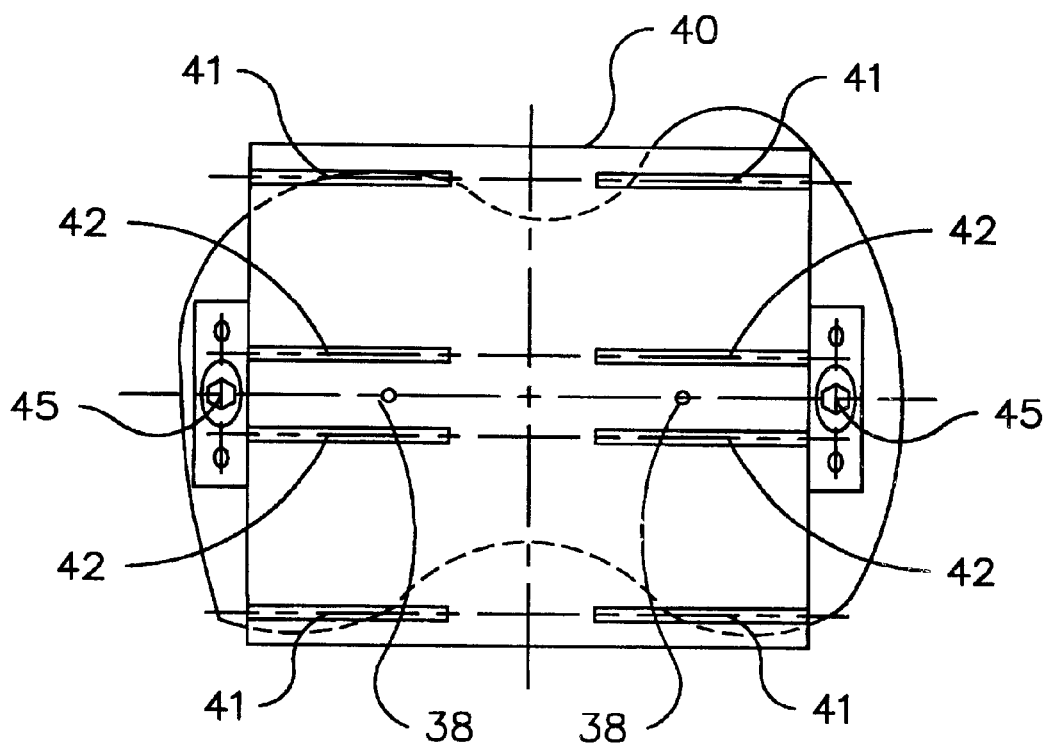
FIG. 3 is the front view of the saw jig attached to the femur stump.

The construction of the nail jig 30 (FIG. 1) and the saw jig 40 (FIGS. 2 and 3) is explained briefly in the following based on the description of FIGS. 1 to 3. The use of the described system should become clearer based on the description of FIGS. 4 and 5.

Figure 1:
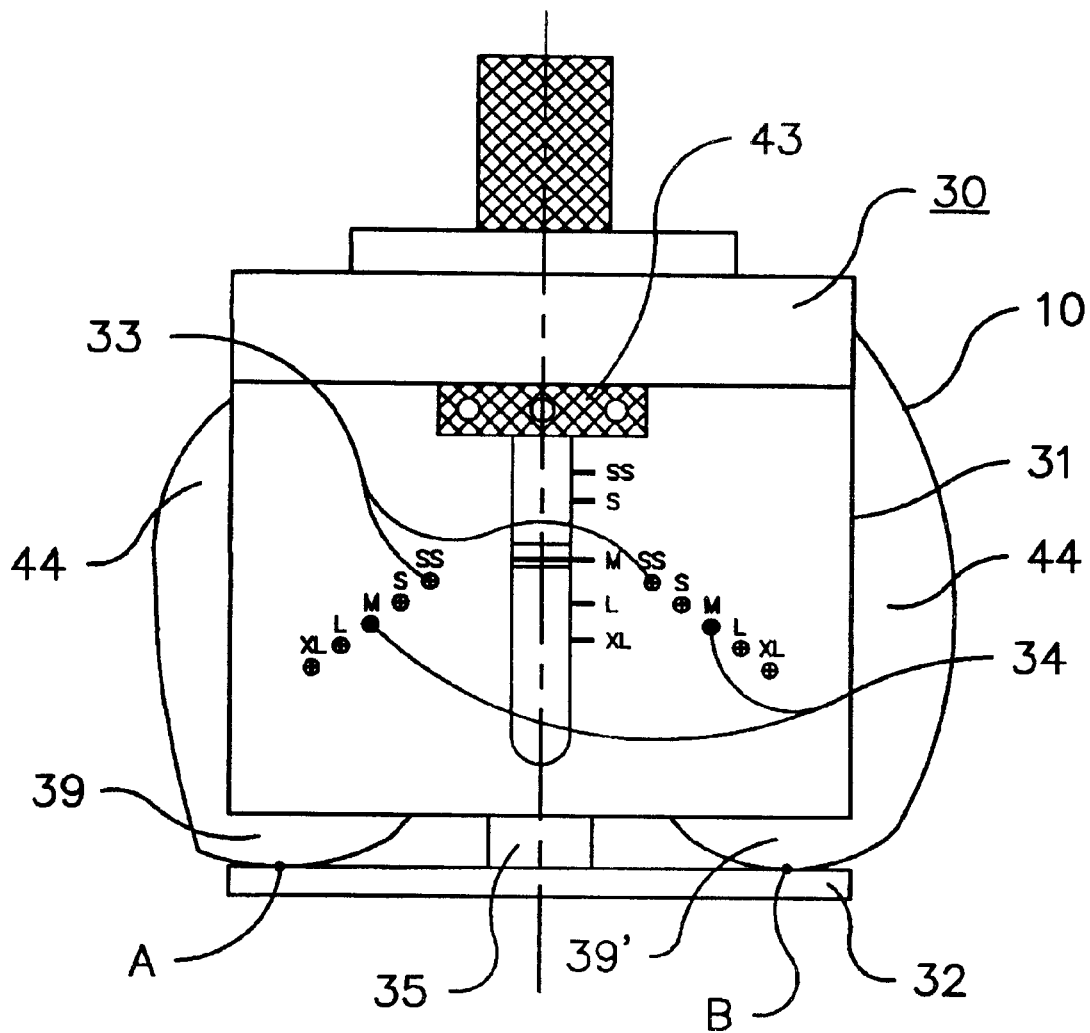
FIG. 1 is a front view of the nail jig, set on the condyles of the natural knee joint.

FIG. 1 shows the front view of the nail jig 30, as it overlaps the condyles 44 of the natural knee joint on the distal end of the femur 10. The nail jig 30 essentially comprises an exactly cuboid-shaped bearing block 31. On the dorsally lying side (i.e., at the bottom in FIG. 1), a striking plate 32 is guided, which contacts the rear condyle rounds 39, 39' only at points A and B. Here, the striking plate 32 is connected to the bearing block via a threaded spindle 35, which acts together with a knurled screw 43 as a gear mechanism in such a way that the distance of the striking plate 32 from the bearing block 31 can be varied, so that the nail jig 30 functions in the manner of a sliding jig (caliper) for the determination of the size of the femur part of the artificial knee joint.

Points A and B form two points for the leveled stable three-point bearing. The third point C (FIG. 4) is the contact point of the femur contact feeler 36 of the nail jig 30. The femur contact feeler 36 is constructed as a bolt stand perpendicularly on a leg 37 pointing toward the femur and projects away from the ventrally lying side face of the bearing block 31. The surgeon must bring the nail jig into a stable three point position with the bearing points A, B and C, after determining the size of the femur part of the implant. Only then is a reference produced to the twist between the knee and the hip region of the patient.

The bearing block 31 is penetrated by a row of drill hole pairs 33, 34, each pair of which corresponds to a certain size of femur part.

After locating the stable three point bearing of the nail jig 30, a respective fixing nail 38 is set into each of the two drill holes of the relevant drill hole pair 33 and 34, after a prior size determination and assignment to the relevant drill hole pair, and the nail is pounded into the femur 10. The fixing nails 38 are here constructed in such a way that the nail jig 30 can be readily pulled away from the femur 10 leaving behind the fixing nails 38 in the femur 10. The fixing nails 38 thus do not have an enlarged head.

Next, the saw jig 40 (FIG. 2) comes into use. The saw jig 40 has available the same drill hole pair pattern as the nail jig 30. The saw jig 40 can accordingly now be set onto the fixing nails 38 remaining in the femur bone. Since the size determination has already been performed previously, the slits 41 for producing the perpendicular sections lie ventrally and dorsally, and the slits 42 for the diagonal sections automatically lie in the proper position on the femur, so that the twist is maintained based on the use of the system. By passing through an oscillating saw blade, the ventral section V, the dorsal section D, and the two diagonal sections Di can be made. Here, the saw jig 40 is still locked on the femur by two additional fixation screws 45 (FIG. 3), so that no displacement of the saw jig 40 can occur due to the sawing operation.

The use of the system is described briefly in the following:

At the beginning of the resection, the horizontal bearing surface H (FIG. 5) is created first. For this purpose, a bearing block 17 is set frontally on the femur 10. A guide spike 11 having a dumbbell 11a penetrates the bearing block 17 and engages into the marrow space of the femur 10. The bearing block 17 is strung, so-to-speak, on the guide spike. A leg 13 pointing toward the femur is provided with a femur contact feeler 15. On the leg 13 a saw jig 14 can be driven in the longitudinal direction of the leg 13. A slit 18 in the saw jig 14 gives the direction and position of the horizontal bearing surface H. An oscillating bone saw is guided through the slit 18. Prior to the use of the saw, however, the saw jig 14 is secured with fixing nails 16 to the femur 10. Then, the bearing block 17 and the guide spike are removed, as is the femur contact feeler 15, and the cut for the horizontal bearing surface H is carried out.

Figure 4:
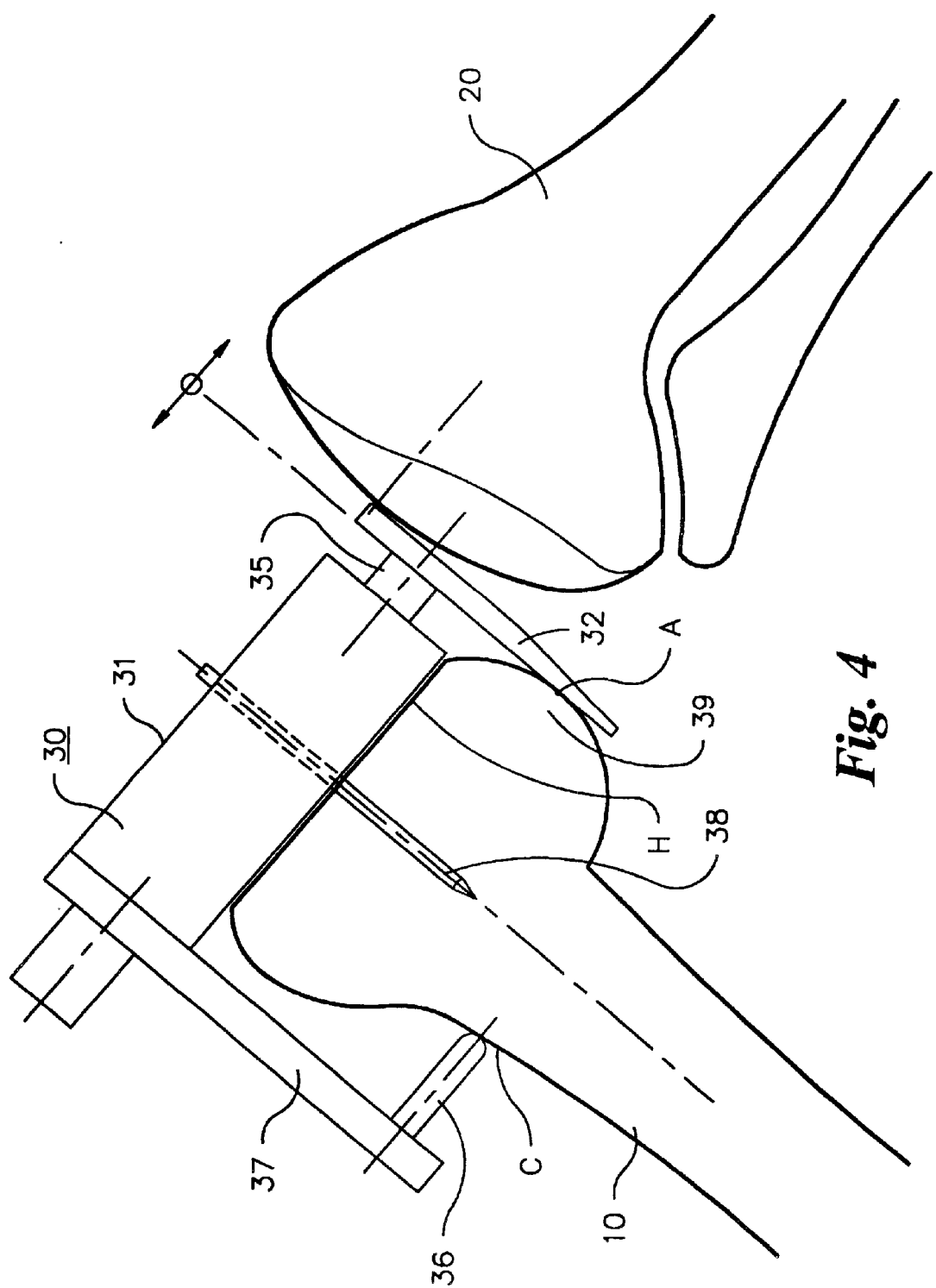
FIG. 4 is the view of the nail jig from the medial, fixed to the horizontal bearing surface of the femur.
Figure 5:
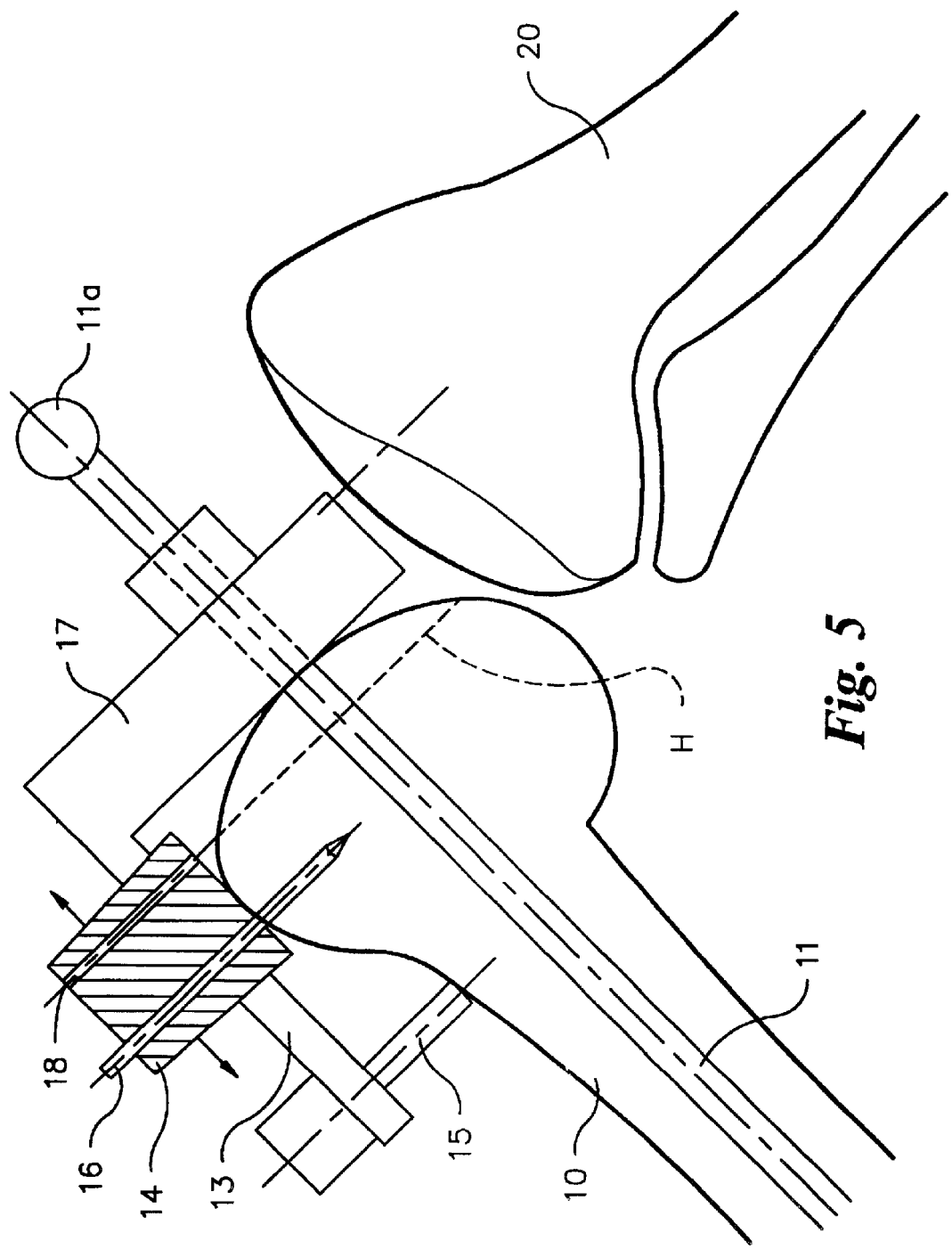
FIG. 5 is the view of the natural knee joint from the medial, prepared for production of the horizontal bearing surface.

After such a preparation the system is ready for use, as is indicated in FIG. 4. Here, the nail jig 30—as constructed—is equipped with a gear mechanism 35 and 43 (FIG. 1), so that it can be pulled in the manner of a sliding caliper for the size determination of the femur part of the artificial knee joint.

For this purpose, the nail jig 30 is first brought back into the stable three point position A, B, and C, so that the striking plate 32 thus contacts the rear condyle rounds 39 and 39' respectively at only one position, just as the femur contact feeler 36 contacts the femur 10 on the opposite side.

The stable three-point bearing is not impaired by a direct contact of the bearing block 31 with the horizontal bearing surface A. After locating the stable three-point position, fixing nails 38 are set into the relevant drill hole pair 33, 34 and struck into the femur 10, whereafter the nail jig can then be pulled away, while leaving the fixing nails 38 behind in the femur 10, and the saw jig 40, as already described based on FIG. 2, can be set on the fixing nails 38, whereafter the remaining resection cuts can be performed.

Based on this, it is thus the object of the present invention to further develop the described system so that it reproduces an exact imitation of the natural twist between the knee and the hips under the prerequisite that the resection cut on the tibia is not a horizontal cut, but rather an inclined cut, which is tilted at an angle between 3 to 5° relative to the horizontal from lateral to medial.

This purpose is achieved by the system according to claim 1. Advantageous further embodiments are set forth in the dependent claims.

Accordingly, it is proposed that the described system have in addition a wedge with a wedge angle $\alpha$, which is slidable between the lateral condyle round and the striking plate of the nail jig for compensation of a wedge angle in which the horizontal tibia section deviates from the knee-gap axis.

Operatively one proceeds now in such a way that first a resection cut is made on the tibia, which deviates from the horizontal in the range of the above-mentioned 3 to 5°, and of course, is sloping away from lateral to medial. Exactly parallel to the tibia resection surface, the femur resection surface is set frontally, and indeed with the prior assistance, for example, of a paralleler according to the German patent 44 23 717. Then, the nail jig according to the main application is put into use. For the compensation of the inclination angle, a push is now made on the lateral contact point between the lateral condyle round and the striking surface of the wedge according to the invention, so that an exact imitation of the natural ratios is produced.

While German patent 44 23 717 starts from connected horizontal frontal resections of both the tibia and the femur, the present system, supplemented by the wedge, starts by using separate resection operations on the tibia and on the femur side, which come even closer to the natural ratios.

On the side of the femur, more bone material is sawed off dorsal-medially than dorsal-laterally. On the whole, the artificial knee joint which has been implanted on or in the tibia and femur bones, prepared using the system according to the invention, turns out to be even more free from strain than was possible until now. The movement progression of the artificial knee joint is hereby optimized—independently, of course, of the type of artificial knee joint used.

Advantageously, the wedge angle $\alpha$ lies in the range of 3 to 5°. This angle correlates with the resection angle on the tibia. 3° is chosen for small knees, 5° on the other hand for larger knees. All values between the two end values are possible.

According to an advantageous further embodiment, it is proposed that the at least one dorsally lying striking plate and the ventrally lying leg are connected using a gear mechanism, by which their spacing from each other can be varied.

In this embodiment, the nail jig can first also be used for size determination of the femur part. In principle, the nail jig functions then as a sliding caliper. The surgeon activates the gear mechanism first, so that the striking plate and the leg are set apart from each other so far that the nail jig can be placed readily over the condyles of the natural knee joint, whereupon the surgeon then activates the gear mechanism so that the mentioned spaced is reduced, until such time as the striking plate and the femur contact feeler contact the femur bones. A scale on the gear mechanism can immediately give the surgeon information about the size of the femur part to be implanted, and thus of the entire knee joint. Also, the selection of the saw jig later depends on the size determination of the femur part, as already mentioned above.

According to a still further embodiment, it can be provided that, seen dorsally, two striking plates are provided in the form of two legs—one for each condyle round—which lie in one plane. In this way, optical control, seen from the dorsal side, is possible in the production of the stable three-point bearing, by which the surgeon can rule out, in particular, that the bearing block of the nail jig comes to rest on the resected horizontal bearing surface of the femur, so that a stable position of the nail jig on the femur bone would already be the result hereby, even if the steps for reproducing the twist have not yet been introduced.

Figure 6:
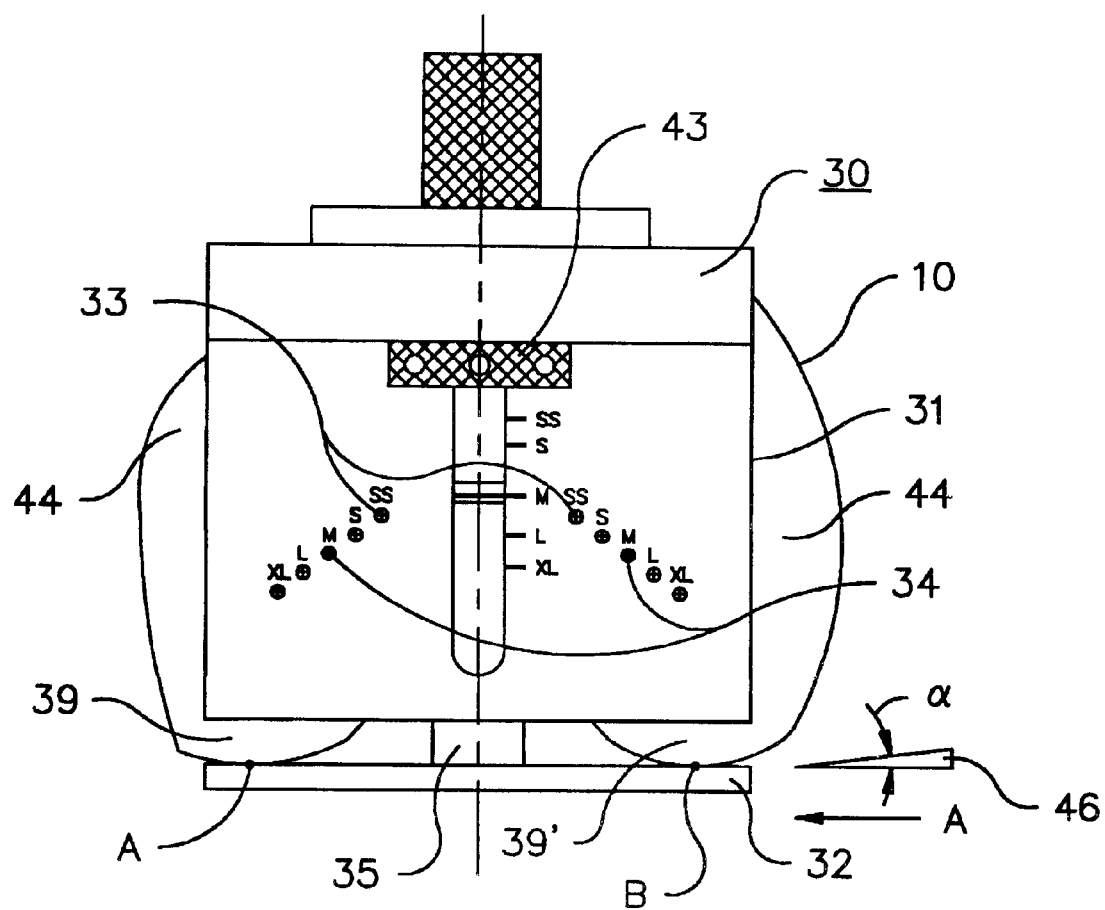
FIG. 6 is a view similar to FIG. 1, but illustrating the method of using the invention.

The invention is explained in greater detail on the basis of an embodiment according to the drawing of FIG. 6.

This drawing shows the front view of the nail jig 30 according to the invention, as it overlaps the femur condyles 44 of the natural knee joint on the distal end of the femur 10. The nail jig 30 essentially comprises an exactly cuboid-shaped bearing block 31. On the dorsally lying side (i.e., at the bottom in the drawing Figure), a striking plate 32 is guided, which contacts the rear condyle rounds 39, 39' only at the points A and B. Here, the striking plate 32 is connected to the bearing block via a threaded spindle 35, which acts together with a knurled screw 43 as a gear mechanism in such a way that the distance of the striking plate 32 from the bearing block 31 can be varied, so that the nail jig 30 functions in the manner of a sliding jig (caliper) for the determination of the size of the femur part of the artificial knee joint. Points A and B form two points for the leveled stable three-point bearing.

The present system has a wedge 46, which is pushed in the direction indicated by the arrow A between the striking plate 32 and the lateral femur condyle 39'. The lateral femur condyle 39' is lifted hereby, since on the whole, a slight rotation is carried out around point A, namely the contact point between the media condyle 39 and the striking plate 32. This rotational movement offers compensation for the inclination of the frontal resection surface on the tibia. The bearing point B is thus shifted from the striking plate 32 up to the wedge 46.

The angle $\alpha$ preferably lies in the range of 3 to 5° and corresponds thus to the inclination of the horizontal resection surface on the tibia.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

I claim:

1. A system for reconstruction of the natural twist between a natural knee and a region of the natural hip in an arrangement between an artificial knee joint and the region of the natural hip after partial resection of the natural condyles of the knee joint and bearing of a femur part of the artificial knee joint of a predetermined size on the resection surfaces of the femur bone, comprising a nail jig (30) with an exactly cuboid-shaped bearing block (31), which has on its end face seen ventrally a leg projecting therefrom and configured for pointing toward the femur, the leg holding on its end a femur contact feeler in a form of a bolt standing perpendicular to the leg for ventrally lying support (C) on the femur (10), and which has on its end face seen dorsally, at least one striking plate (32) projecting therefrom and configured for pointing toward the femur for respective dorsal lying support (A, B) on both dorsal condyle rounds (39, 39'), wherein the bearing block (31) has drill hole pairs (33, 34) passing therethrough, whose arrangement represents the respective size of the femur part, and through which fixing nails are insertable, which secure the bearing block (31) in its position on the femur (10), and wherein the bearing block (31) can be pulled away from the femur while leaving behind the fixing nails, and a saw jig having an identical basic shape as the bearing block (31) of the nail jig (30) and having an identical arrangement of drill hole pairs in the bearing block (31), which can be set on the fixing nails, so that its end faces define resection planes, and further having a wedge with a wedge angle $\alpha$, which can be pushed between the lateral condyle round (39') and the striking plate (32) for compensation of a wedge angle, by which the horizontal tibia section deviates from the knee gap axis.

2. The system according to claim 1, wherein the wedge angle $\alpha$ lies in a range of $3° \leq \alpha \leq 5°$.

3. The system according to claim 1, wherein the dorsally lying striking plate (32) and the ventrally lying leg (37) of the nail jig (30) are connected by a gear mechanism (35, 43), by which their distance from each other can be varied.

4. The system according to claim 1, wherein two striking plates are provided dorsally in a form of two legs, which lie in one plane.

* * * * *